United States Patent [19]

Dawes et al.

[11] 3,932,629
[45] Jan. 13, 1976

[54] TRIAZOLYL PHOSPHORUS ESTERS AS PESTICIDES

[75] Inventors: Dag Dawes, Pratteln; Beat Böhner, Binningen, both of Switzerland

[73] Assignee: Ciba-Geigy Corporation, Ardsley, N.Y.

[22] Filed: Dec. 6, 1974

[21] Appl. No.: 530,460

Related U.S. Application Data

[62] Division of Ser. No. 310,530, Nov. 29, 1972, Pat. No. 3,867,396.

[30] Foreign Application Priority Data

Dec. 10, 1971  Switzerland.................... 18065/71
Sept. 29, 1972  Switzerland.................... 14254/72

[52] U.S. Cl. .................................................. 424/200
[51] Int. Cl.² ............................................. A01N 9/36
[58] Field of Search ..................................... 424/200

[56] References Cited
UNITED STATES PATENTS

| | | |
|---|---|---|
| 3,686,200 | 8/1972 | Scherer et al. ............... 424/200 |
| 3,809,701 | 5/1974 | Dawes et al. ................ 424/200 |
| 3,862,124 | 1/1975 | Dawes et al. ................ 424/200 |
| 3,862,170 | 1/1975 | Dawes et al. ................ 424/200 |
| 3,862,957 | 1/1975 | Dawes et al. ................ 424/200 |

FOREIGN PATENTS OR APPLICATIONS 2,057,170  5/1971  Germany .................. 260/308

OTHER PUBLICATIONS

Chem. Abst. 71, 101861(c) (1969) – Scherer et al. abstracting So. African 6803,471, Oct. 31, 1968.

Primary Examiner—Albert T. Meyers
Assistant Examiner—D. W. Robinson
Attorney, Agent, or Firm—Harry Falber

[57] ABSTRACT

Triazolylorganophosphorous derivatives of the formula

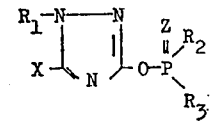

wherein X represents fluorine, chlorine or bromine, Z represents oxygen or sulphur, $R_1$ represents alkyl, cycloalkyl, unsubstituted or substituted aryl or aralkyl, $R_2$ represents alkoxy, alkylthio, amino, mono- or dialkylamino and $R_3$ represents alkyl, alkoxy, alkylthio, phenyl, phenoxy, amino, mono- or dialkylamino, a process for their manufacture and their use in pest control.

10 Claims, No Drawings

TRIAZOLYL PHOSPHORUS ESTERS AS PESTICIDES

This is a division of application Ser. No. 310,530, filed on Nov. 29, 1972, now U.S. Pat. No. 3,867,396.

The present invention relates to triazolylorganophosphourus derivatives, a process for their manufacture and their use in pest control.

The compounds have the formula

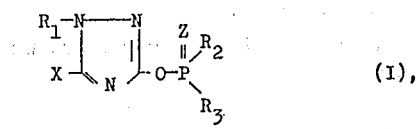

wherein X represents fluorine, chlorine or bromine, Z represents oxygen or sulphur, $R_1$ represents alkyl, cycloalkyl, unsubstituted or substituted aryl or aralkyl, $R_2$ represents alkoxy, alkylthio, amino, mono- or dialkylamino and $R_3$ represents alkyl, alkoxy, alkylthio, phenyl, phenoxy, amino, mono- or dialkylamino.

The alkyl, alkoxy and alkylthio groups represented by $R_1$ to $R_3$ contain in the chain 1 to 19, preferably 1 to 6, carbon atoms and may be straight-chain or branched, unsubstituted or optionally substituted by halogen atoms, such as fluorine, chlorine, bromine and/or iodine.

Examples of such groups include methyl, methoxy, methylthio, ethyl, ethoxy, ethylthio, 2-chloroethyl, propyl, 3,3,3-trichloropropyl, propoxy, propylthio, isopropyl, N-, 1-, sec. and tert.butyl, 4-chloro-(n)-butyl, n-pentyl, n-dodecyl, (n)-nonadecyl.

The cycloalkyl groups represented by $R_1$ contain 3 to 8, but preferably 5 to 6, ring carbon atoms. Examples of such groups are cyclopentyl and cyclohexyl.

The aralkyl radical represented by $R_1$ is preferably a benzyl, phenethyl or diphenylmethyl group or is a group of the formula

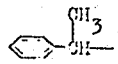

and the aryl radical is a carboxylic, aromatic ring in particular the phenyl ring.

The aralkyl, in particular the benzyl and aryl, especially phenyl, groups may be unsubstituted or substituted.

Possible substitutents at these groups are preferably fluorine, chlorine and/or bromine, alkyl and haloalkyl each with 1 to 6 carbon atoms, in particular —$CF_3$, alkoxy, alkylsulphinyl, and alkylsulphonyl, each with 1 to 6 carbon atoms, and/or nitro groups.

Preferred compounds on account of their action are those of the formula I, wherein X represents chlorine or bromine, Z represents oxygen or sulphur, $R_1$ represents alkyl with 1 to 19 carbon atoms, cyclopentyl, phenyl or benzyl which is unsubstituted or mono- or polysubstituted by fluorine, chlorine, bromine, methyl, trifluoromethyl, methoxy, methylthio, ethoxy and/or nitro, phenethyl, diphenylmethyl or

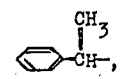

$R_2$ represents methoxy, ethoxy, propoxy, 2-chloroethoxy, propylthio, methylamino, dimethylamino or isopropylamino, and $R_3$ represents methyl, ethyl, methoxy, methylthio, ethoxy, ethylthio, propxy, 2-chloroethoxy, propylthio, phenyl, phenoxy, amino, methylamino or dimethylamino.

Particular repreferred compounds, however, are those of the formula I, wherein X represents chlorine, Z represents sulphur, $R_1$ represents alkyl with 1 to 6 carbon atoms, cyclopentyl, phenyl, 3-trifluoromethylphenyl, benzyl, diphenylmethyl or

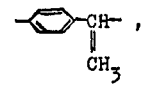

$R_2$ represents methoxy, ethoxy or propoxy, and $R_3$ represents methyl, ethyl, methoxy, ethoxy, propylthio, amino, methylamino and dimethylamino.

The compounds according to the invention of the formula 1 a I can be manufactured by methoxy which are known per se.

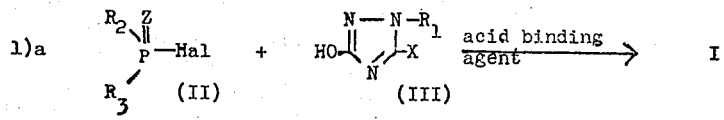

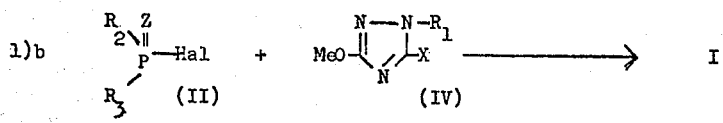

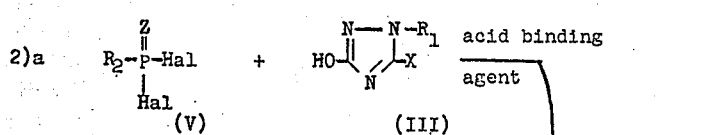

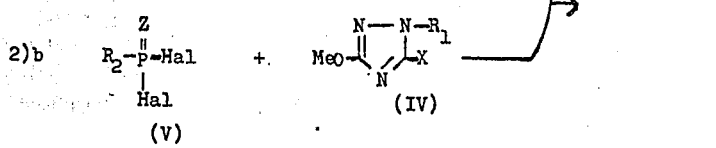

-continued

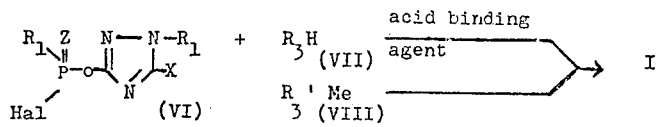

In the formulae II to VIII, the symbols $R_1$ to R, X and Z, have the meanings given for the formula I, Hal represents fluorine, chlorine, bromine, or iodine, but in particular chlorine or bromine, $R_3'$ ≈ — represents alkoxy, ethylthio or phenoxy, and Me represents a momovalent metal, preferably an alkali metal, in particular sodium or potassium.

In the formulae II to VIII, the symbols $R_1$ to R, X and Z have the meanings given for the formula I, Hal represents fluorine, chlorine, bromine or iodine, but in particular chlorine or bromine, $R_3'$ represents alkoxy, ethylthio or phenoxy, and Me represents a monovalent metal, preferably an alkali metal, in particular sodium or potassium.

The following bases, for example, are suitable as acid binding agents, tertiary amines, such as triethylamine, dimethylaniline, pyridine, inorganic bases, such as hydroxides and carbonates of alkali and alkaline earth metals, preferably sodium and potassium hydroxide.

The reaction may be carried out preferably in solvents or diluents which are inert towards the reactants or in an excess of a tertiary amine, e.g. pyridine. Suitable inert solvents or diluents are, for example, the following: aromatic hydrocarbons, such as benzene, toluene, benzines, halogenated hydrocarbons, chlorobenzene, polychlorobenzenes, bromobenzene, chlorinated alkanes with 1 to 3 carbon atoms, ethers, such as dioxan, tetrahydrofuran; esters, such as ethyl acetate; ketones, such as methyl ethyl ketone, diethyl ketone, nitriles etc.

The starting materials of the formulae III to IV are new and can be manufactured, for example, by halogenation or transhalogenation of 3-hydroxy-triazole derivatives which are unsubstituted in the 5-position, or esters thereof.

The compounds of the formula I display a broad biocidal activity and are therefore suitable for combating various plant and animal pests.

In particular, the compounds of the formula I possess insecticidal and acaricidal properties and may be used against all development stages, e.g. eggs, larvae, pupae, nymphs and adults, of insects and representatives of the order Acarina, for example against insects of the families:

| | |
|---|---|
| *Tattigonidae* | *Tenebrionidae* |
| *Gryllidae* | *Chrysomelidae* |
| *Gryllotalpidae* | *Bruchidae* |
| *Blattidae* | *Tineidae* |
| *Reduviidae* | *Noctuidae* |
| *Phyrrhocoriae* | *Lymatriidae* |
| *Cimicidae* | *Pyralidae* |
| *Delphacidae* | *Culicidae* |
| *Aphididae* | *Tipulidae* |
| *Diaspididae* | *Stomoxydae* |
| *Pseudococcidae* | *Trypetidae* |
| *Scarabacidae* | *Muscidae* |
| *Dermestidae* | *Calliphoridae* and |
| *Coccinellidae* | *Pulicidae* |

Acarida of the families:
Ixodidae
Argasidae
Tetranychidae and
Dermanyssidae.

The insecticidal and/or acaricidal action can be substantially broadened and adapted to suit the particular circumstances by the addition of other insecticides and/or acaricides.

Suitable additives include, for example, the following active substances:

Bis- O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethyl-phosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4-5-trichlorophenylthiophosphate (RONNEL)
O-ethyl-O,2,4,5-trichlorophenylethylthiophosphate (TRICHLORONATE)
O,O-dimethyl-O-2,5-dichloro-4-bromophenylthiophosphate (BROMOPHOS)
O,O-dimethyl-O-(2,5-dichloro-4-jodphenyl)-thiophosphate (JODOFENPHOS)
4-tert. butyl-2-chlorophenyl-N-methyl-O-methylamidophosphate (CRUFOMATE)
O,O-dimethyl-O-(3-methyl-4-methylmercaptophenyl)-thiophosphate (FENTHION)

Isopropylamino-O-ethyl-O-(4-methylmercapto-3-methylphenyl)-phosphate
O,O-diethyl-O-p-(methylsulphinyl)phenyl-thiophosphate (FENSULFOTHION)
O-p-(dimethylsulphamido)phenyl-O,O-dimethylthiophosphate (FAMPHUR)
O,O,O',O'-tetramethyl-O,O'-thiodi-p-phenylenethiophosphate O-ethyl-S-phenyl-ethyldithiophosphate
O-ethyl-S-phenyl-ethyldithiophosphate
O,O-dimethyl-O-(α-methylbenzyl-3-hydroxycrotonyl)-phosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
O-[2-chloro-1-(2,5-dichlorophenyl)]vinyl-O,O-diethylthiophosphate
Phenylglyoxylonitriloxim-O,O-diethylthiophosphate (PHOXIM)
O,O-diethyl-O-(3-chloro-4-methyl-2-oxo-2-H-1-benzopyran-7-yl)thiophosphate (COUMAPHOS)
2,3-p-dioxandithiol-S,S-bis(O,O-diethyldithiophosphate) (DIOXATHION)
5-[(6-chloro-2-oxo-3-benzoxazolinyl)methyl]O,O-diethyldithiophsophate (PHOSALONE)
2-(diethoxyphosphinylimino)-1,3-dithiolane
O,O-dimethyl-S-[2-methoxy-1,3,4-thiadiazol -5-(4H)-onyl-(4)-methyl]dithiophosphate
O,O-dimethyl-S-phtha(imidomethyl-dithiophosphate (IMIDAN)
O,O-diethyl-O-(3,5,6-trichloro-2-pyridyl)thiophosphate
O,O-diethyl-O2-pyrazinylthiophosphate (THIONAZIN)
O,O-diethyl-O-(2-isopropyl-4-methyl-6-pyrimidyl)thiophosphate (DIAZINON)
O,O-diethyl-O-(2-chinoxalyl)thiophosphate
O,O-dimethyl-S-(4-oxo-1,2,3-benzotriazin-3(4H)-ylmethyl)dithiophosphate (AZINPHOSMETHYL)
O,O-diethyl-S-(4-oxo-1,2,3-benzotriazin-3(4H)-ylmethyl)dithiophosphate (AZINPHOSETHYL)
S-[(4,6-diamino-s-triazin-2-yl)methyl]-O,O-dimethyl-dithiophosphate (MENAZON)
O,O-dimethyl-O-(3-chloro-4-nitrophenyl)thiophosphate (CHLORTHION)
O,O-dimethyl-O(or S)-2-(ethylthioethyl)thiophosphate (DEMETONS-METHYL)
2-(O,O-dimethyl-phosphoryl-thiomethyl)-5-methoxy-pyron-4-3,4-dichlorobenzyl-triphenylphosphoniumchloride
O,O-diethyl-S-(2,5-dichlorophenylthiomethyl)dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1-1,2,4-triazole (TRIAMIPHOS)
N-methyl-5-(O,O-dimethylthiolphosphoryl)-3-thiavaleramide (VAMIDOTHION)
O,O-diethyl-O-[2-diemthylamino-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-dimethyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-O,O-dimethyldithiophosphate
Hexamethylphosphoric acid triamide (HEMPA)
O,O-dimethyl-O-(2-chloro-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O-2,4-dichlorophenylthiophosphate (DICHLORFENTHION)
O,2,4-dichlorophenyl-O-methylisopropylamidothiophosphate
O,O-diethyl-O-2,5-dichloro-4-bromophenylthiophosphate (BROMOPHOS-ETHYL)
Dimethyl-p-(methylthio)phenylphosphate
O,O-dimethyl-O-p-sulfamidophenylthiophosphate
O-[p-(p-chlorophenyl)azophenyl]O,O-dimethylthiophosphate (AZOTHOATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyl-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)2-methoxy-4-H-1,3,2-benzodioxaphosphorin-2-sulphide
O,O-diethyl-O-(5-phenyl-3-isooxazolyl)thiophosphate
2-(diethoxyphosphinylimino)-4-methyl-1,3-dithiolane
Tris-(2-methyl-1-aziridinyl)-phosphine oxide (METEPA)
S-(2-chloro-1-phthalimidoethyl)-O,O-diethyldithiophosphate
N-hydroxynapthalimido-diethylphosphate
Dimethyl-3,5,6-trichloro-2-pyridylphosphate
O,O-dimethyl-O-(3,5,6-trichloro-2pyridyl)thiophosphate
S-2-(ethylsulphonyl)ethyl dimethylthiolphosphate (DIOXYDEMETON-S-METHYL)
Diethyl-S-2-(ethylsulphinyl)ethyl dithiophosphate (OXIDISULFOTON)
Bis-O,O-diethylthiophosphoric acid anhydride (SULFOTEP)
Dimethyl-1,3-di(carbomethoxy)-1-propen-2-yl-phosphate
Dimethyl-(2,2,2-trichloro-1-butyroyloxyethyl)phosphate (BUTONATE)
O,O-dimethyl-O-(2,2-dichloro-1-methoxy-vinyl)phosphate
Bis-(dimethylamido)fluorphosphate (DIMEFOX)
3,4-dichlorobenzyl-triphenylphosphiumchloride Dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)-phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
Diisopropylaminofluorophosphate (MIPAFOX)
O,O-dimethyl-S-(morpholinylcarbamoylmethyl)dithiophosphate (MORPHOTHION)
Bismethylamido-phenylphosphate
O,O-dimethyl-S-(benzene sulphonyl)dithiophosphate
O,O-dimethyl-(S and O)-ethylsulphinylethylthiophosphate
O,O-diethyl-O- 4-nitrophenylphosphate
Triethoxy-isopropoxy-bis(thiophosphinyl)disulphide
2-methoxy-4H-1,3,2, benzodioxaphosphorin-2-oxide
Octamethylpyrophosphoramide (SCHRADAN)
Bis (dimethoxythiospphinylsulphido)-phenylmethane
N,N,N', N'-tetramethyldiamidofluorophosphate (DIMEFOX)
O-phenyl-O-p-nitrophenyl-methanthiophosphonate (COLEP)
O-methyl-O-(2-chloro-4-tert.butyl-phenyl)-N-methylamidothiophosphate (MARLFNE)
O-ethyl-O-(2,4-dichlorophenyl)-phenylthiophosphonate
O,O-diethyl-O-(4-methylmercapto-3,5-dimethylphenyl)-thiophosphate
4,4'-bis-(O,O-dimethylthiophosphoryloxy)-diphenyl disulphide
O,O-di-(β-chloroethyl)-O-(3-chloro-4-methyl-coumarinyl-7)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2-carbispropoxyphenyl)-amidothiophosphate
5-(O,O-dimethylphosphoryl)-6-chloro-bicyclo(3.2.0)-heptadiene(1,5)
O-methyl-O-(2-i-propoxycarbonyl-1-methylvinyl)-ethylamido-thiophosphate.

Nitrophenols and derivatives 4,6-dinitro-6-methylphenol, Na-salt [Dinitrocresol]
dinitrobutylphenol-(2,2',2''-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous pyrethin I
pyrethin II
3-allyl-2-methyl-4-oxo-2-cyclopentan-1-yl-chrysanthemumate (Allethrin)
6-chloriperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxol, 3-dithiolo-[4,5-b]-qunioxaline (Quinomethionate)
(I)-3-(2-furfuryl)-2-methyl-4-oxocyclopent-2-enyl(I-(cis+trans)-chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbanyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(,5-6)-quinoxaline -qunioxaline [Thiochinox]
prop-2-ynyl-(4-t-butylphenoxy)cyclohexylsulphite [Propargil].

Formamidines 1-dimethyl-2-(2'-methyl-4'-chlorophenyl)-formamidine (CHLORPHENAMIDIN)
1-methyl-2-(2'methyl-4'-chlorophenyl)-formamidine
1-methyl-2-(2'-methyl-4'-bromophenyl)-formamidine
1-methyl-2-(2', 4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl)-formamidine
1-n-butyl-2-(2'-methyl-4'-chlorophenyl-imino)-pyrolidine.

Urea

N-2-methyl-4-chlorophenyl-N', N'-dimethyl-thiourea.

Carbamate 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-O-)methylcarbamoyl)-oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-O-(methylcarbamoyl)-oxime (ALDICARB)

8-chinaldyl-N-methylcarbamate and their salts
methyl 2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate
3,4-dimethylphenyl-N-methylcarbamate
2-cyclopentylphenyl-N-methylcarbamate
3-dimethylamino-methyleneiminophenyl-N-methylcarbamate(FORMETANATE) and their salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-0-methylcarbamyl-formoxime
1-(2'-cyanoethylthio)-0-methylcarbamyl-acetaldoxime
1-methylthio-0-carbamyl-acetaldoxime
0-(3-sec.butylphenyl)-N-phenylthio-N-methylcarbamate
2,5-dimethyl-1,3-dithioland-2-(0-methylcarbamyl)-aldoxime)
0-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetyl-carbamate
3-isopropylphenyl-N-methyl-N-methylthiomethyl-carbamate
0-(2,2-dimethyl-4-chloro-2,3-dihydro-7-benzofuranyl)-N-methylcarbamate
0-(2,2,4-trimethyl-2,3-dihydro-7-benzofuranyl)-N-methylcarbamate
0-naphthyl-N-methyl-N-acetyl-carbamate
0-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-$\gamma$-methylthiopropylphenyl-N-methyl-carbamate
3-($\alpha$-methoxymethyl-2-propenyl)-phenyl-N-methyl-carbamate
2-chloro-5-tert.-butyl-phenyl-N-methyl-carbamate
4-(methyl-propargylamino)-3,5-xylyl-N-methyl-carbamate
4-(methyl-$\gamma$-chloroallylamino)-3,5-xylyl-N-methyl-carbamate
4-(methyl-$\beta$-chloroallylamino)-3,5-xylyl-N-methyl-carbamate
1-($\beta$-ethoxycarbonalethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
2-[dipropargylamino]-phenyl-N-methylcarbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate Chlorinated Hydrocarbons $\gamma$-hexachlorocyclohexane [GAMMEXANE; LINDAN; $\gamma$HCH]
1,2,4,5,6,7,8,8-octachloro-3$\alpha$,4,7,7$\alpha$'tetrahydro-4,7-methylenindane [CHLORDAN]
1,4,5,6,7,8,8-heptachloro,3$\alpha$,4,7,7$\alpha$-tetrahydro-4,7-methylenindane [HEPTACHLOR]
1,2,3,4,10,10-hexachloro-1,4,4$\alpha$,5,8,8$\alpha$-hexahydro-endo-1,4-exo-5,8-dimethanonaphthalene [ALDRIN]
1,2,3,4,10,10-hexachloro-6,7-epoxy-1,4,4$\alpha$,5,6,7,8,8$\alpha$-oxtahydro-exo-1,4-endo-5,8-dimethanonaphthalene [DIFLORIN]
1,2,3,4,10,10-hexachloro-5,7-epoxy-1,4,4$\alpha$,5,6,7,8,8$\alpha$-octyhydro-endo-endo-5,8-dimethanonaphthalene [ENDRIN]

The active substances of the formula I are also suitable for combating representatives of the division Thallophyta, e.g. viruses, bacteria and fungi. They thus possess fungicidal properties against phytopathogenic fungi on various cultivated plants, such as cereals, maize, rice, vegetables, ornamental plants, fruit trees, vines, farm products, etc.

With the new active substances it is possible to control or destroy fungi occurring on fruit, blossom, leaves, stems, tubers and roots, and from which parts of plants which grow later then also remain free. The active substances of the formula I are active in particular against phytopahtogenic fungi belonging to the following classes: Oomycetes, Zygomycetes, Ascomycetes, Basidiomycetes, Denteromycetes.

In addition, the new active substances can also be used for treating seeds, fruit, tubers etc., and the protecting them from fungus infections, for example from smut fungi of all kinds, such as Ustilaginales, e.g. Ustilago, Tilletia, Urocystis, Turbicinia and Phoma types.

In addition to the above cited acaricides and insecticides, it is also possible to admix the active substances of the formula I with, for example, bactericides, fungistatic agents, baceteriostatic agents, nematocides and/or e.g. the following fungicides, in order to broaden the activity spectrum:

dodecylquanidine acetate (DODINE)
pentachloronitrobenzene (QUINTOZENE)
pentachlorophenol (PCP)
2-(1-methyl-n-propyl)-4,6-dinitrophenyl-2-methyl-crotonate (BINAPACRYL)
2-(1-methyl-n-heptyl)-4,6-dinitrophenylcrotonate (DINOCAP)
2,6-dichloro-4-nitroaniline (DICHLORAN)
2,3,5,6-tetrachloro-benzoquinone (1,4) (CHLORANIL)
2,3-dichloro-naphthoquinone (1,4) (DICHLONE)
N-(trichloromethylthio) phthalimide (FOLPET)
N-(trichloromethylthio) cyclohex-4-en-1,2-dicarboximide (CAPTAN)
N-(1,1,2,2-tetrachloroethylthio)cyclohex-4-en-1,2-dicarboximide (CAPTAFOL)
N-methansulfonal-N-trichloromethylthio-chloroaniline
N'-dichlorofluoromethylthio-N,N-dimethyl-N'-phenyl-sulfamide (DICHLOFLUANID)
O-ethyl-S-benzyl-phenyldithiophosphate
O,O-diethyl-S-benzyl-thiolphosphate
disodium-ethylene-1,2-bis-dithiocarbamate (NABAM)
zinc-ethylene-1,2-bis-dithiocarbamate (ZINEB)
manganese-ethylene-1,2-bis-dithiocarbamate (polymeric) (MANEB)
tetramethylthiuramdisulfide (THIRAM)
1-oxy-3-acetyl-6-methyl-cyclohexene-(5)dione-(2,4) (DEHYDROACETIC ACID)
8-hydroxyquinoline (8-QUINOLINOL)
2-dimethylamino-6-methyl-5-n-butyl-4-hydroxy-pyrimidine
methyl-N-benzimidazole-2-yl-N-(butylcarbamoyl)carbamate (BENOMYL)
2-ethylamino-6-methyl-5n-butyl-4-hydroxypyrimidine
2,3-dicyano-1,4-dithia-anthraquinone (DITHIANON)
2-(4-thiazolyl)-benzimidazole
3,5-dimethyltetrahydro-1,3,5-thiadiazine-2-thione (DAZOMET)
2,3-dihydro-5-carboxanilido-6-methyl-1,4-oxathine
pentachlorobenzyl alcohol.

Furthermore, the compounds of the formula I are suitable for combating plant pathogenic nematodes.

The compounds of the formula I may be used as pure active substance or together with suitable carriers and/or additives. Suitable carriers and additives can be solid or liquid and correspond to the substances conventionally used in formulation technique such, for example, as solvents dispersants, wetting agents, adhesives, thickeners, binders and/or fertilisers.

For application, the compounds of the formula I may be processed to dusts, emulsion concentrates, granules, dispersions, sprays, to solutions, or suspensions in the conventional formulation which is commonly employed in application technology. Mention may also be made of "cattle dips" and "spray races", in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take and be used in the following forms:

Solid forms:
Dusts, tracking agents, granules, coated granules, impregnated granules and homogeneous granules.

Liquid forms:
a. active substances which are dispersible in water: wettable powders, pasts, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivates (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove in such a manner that, in wettable powders, the solid particle size of from 0.02 to 0.04 and in pastes, of 0.03 is not exceeded. To produce emulsifiable concentrates and pastes, dispersing agents such as those cited above, organic solvents and water are used. Examples of suitable solvents are: alcohols, benzene, xylene, toluene, dimethyl sulfoxide, and mineral oil fractions boiling between 120° and 350°C. The solvents must be practically odourless, not phytotoxic, inert to the active substances.

Furthermore, the agents according to the invention can be applied in the form of solutions. For this purpose the active substance or several active substances of the general formula I are dissolved in suitable organic solvents, mixtures of solvents or in water. Aliphatic and aromatic hydrocarbons, chlorinated derivatives thereof, alkyl naphthalenes, and mineral oils singly or in admixture with each other, can be used as organic solvents.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:
a. 5 parts of active substance
   95 parts of talcum
   2 parts of active substance
   1 part of highly disperse silica
   97 parts of talcum.

The active substances are mixed with the carriers and ground.

Granules

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder:

The following constituents are used for the preparation of (a) a 40%, (b) and (c) a 25%, and (d) a 10% wettable powder:
a. 40 parts of active substance,
   5 parts of sodium lignin sulphonate,
   1 part of sodium dibutyl-naphthalene sulphonate,
   54 parts of silica acid.
b. 25 parts of active substance,
   4.5 parts of calcium lignin sulphonate
   1.9 parts of Champagne chalk/hydroxyethyl cellulose mixture (1:1),
   1.5 parts of sodium dibutyl naphthalene sulphonate,
   19.5 parts of silica acid,
   19.5 parts of Champagne chalk,
   28.1 parts of kaolin.
c. 25 parts of active substance,
   2.5 parts of isooctylphenoxy-polyoxyethyleneethanol,
   2.7 parts of Champagne chalk/hydroxyethyl cellulose mixture (1:1),
   8.3 parts of sodium aluminium silicate,
   16.5 parts of kieselguhr,
   46 parts of kaolin.
d. 10 parts of active substance,
   3 parts of a mixture of the sodium salts of saturated fatty alcohol sulphates,
   5 parts of naphthalenesulphonic acid/formaldehyde condensate,
   82 parts of kaolin.

The active substances are intimately mixed, in suitable mixers, with the additives, the mixture being then ground in the appropriate mills and rollers. Wettable powder are obtained which can be diluted with water to give suspensions of any desired concentration.

Emulsifiable concentrates:

The following substances are used to produce (a) a 10% and (b) a 25% emulsifiable concentrate:

a. 10 parts of active substance,
3.4 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene.

b. 25 parts of active substance,
2.5 parts of epoxidised vegetable oil,
10 parts of an alkylarylsulphonate/fatty alcohol-polyglycol ether mixture
5 parts of dimethylformamide,
57.5 parts of xylene.

From these concentrates it is possible to produce, by dilution with water, emulsions of any desired concentration.

Spray:
The following constituents are used to prepare a 5% spray:
5 parts of active substance,
1 part of epichlorohydrin,
94 parts of benzine (boiling limits 160° – 190°C).

EXAMPLE 1

Manufacture of the Starting Material a. 1-isopropyl-5-chloro-3-hydroxy-1,2,4-triazole 127 g of 1-isopropyl-3-hydroxy-1,2,4-triazole and 276 ml of triethylamine are dissolved in 1200 ml of absolute alcohol. The solution turns cloudy yellow. While cooling (26° to 30°C), 106.5 g of chlorine (dried by concentrated sulphuric acid) are passed in within 30 minutes. In the process, the yellow solution initially becomes clear. Subsequently triethylamine hydrochloride precipitates as crystalline product, which is filtered off after stirring for 1 further hour. The filtrate is concentrated to dryness in a rotary evaporator. The brown residue is dissolved in 1 liter of water and 1 liter of ether. The mixture is extracted and separated in a separating funnel. The aqueous phase is extracted three times with 500 ml of ether on each occasion. The combined ether phases are dried over sodium sulphate, the drying agent is filtered off and the filtrate is concentrated to dryness. The light brown residue is dissolved in 500 ml of carbon tetrachloride containing activated charcoal, whereupon the mother liquor is concentrated to ⅓ of its volume and then cooled. The active substance crystallises out and is dried in vacuo for 15 hours at 60°C/15 mm Hg. Yield: 96.3 g (60 % of theory); m.p. : 103°–105°C.

b. 1-phenyl-5-chloro-3-hydroxy-1,2,4-triazole 32.2 g of 1-phenyl-3-hydroxy-1,2,4-triazole and 40.5 g of triethylamine are dissolved in 300 ml of absolute alcohol. While cooling, 21.3 g of chlorine are passed in (20° to 30°C). Triethylamino hydrochloride is filtered off and the filtrate is concentrated in a rotary evaporator. The residue is treated with 300 ml of water and extracted 4 times with 200 ml of ether each time. The combined ethereal extracts are dried over sodium sulphate. The drying agent is filtered off and the filtrate concentrated. The solid residue is recrystallised from 70 ml of acetonitrile. Yield: 11.4 g (29.2 % of theory); m.p. 147°–149°C.

c. 1-phenyl-5-chloro-3-hydroxy-1,2,4-triazole 32.2 g of 1-phenyl-3-hydroxy-1,2,4-triazole and 40.5 g of triethylamine in 300 ml of dimethyl formamide. While cooling with ice, 21.3 g of chlorine gas are passed in at 20° to 30°C. Subsequently the resulting triethylamine hydrochloride is filtered off and the solvent is distilled off in vacuo. The residue is taken up in 300 ml of water and extracted 4 times with 200 ml of ether. The combined ethereal extracts are dried over sodium sulphate and, after the solvent has been filtered off, concentrated in vacuo. The residue is recrystallised from acetonitrile. Yield: 15.0 g (38.4 % of theory); m.p. 146°–147°C.

d. 1-ethyl-5-chloro-3-hydroxy-1,2,4-triazole 71.5 g of chlorine is passed into a solution of 75.5 g of 1-ethyl-3-hydroxy-1,2,4-triazole and 185 ml of triethylamine in 800 ml of absolute ethanol. The exothermic reaction is kept at 20° to 30°C while cooling. Triethylamine hydrochloride is precipitated. The batch is further stirred for 2 hours after the chlorine has been passed in. Triethylamine hydrochloride is filtered off and the filtrate concentrated. The residue is dissolved in 500 ml of ether and 500 ml of water. The phases are separated and the aqueous phase is extracted 3 times with 300 ml of ether each time. The ethereal extracts are dried over sodium sulphate. The drying agent is filtered off and the filtrate concentrated. The residue is recrystallised from a mixture of 400 ml of xylene and 250 ml of ligroin and dried in vacuo. Yield: 28.7 g (29 % of theory); m.p. 108°–110°C.

e. 1-isobutyl-5-chloro-3-hydroxy-1,2,4-triazole 241 g of 1-isobutyl-3-hydroxy-1,2,4-triazole and 475 ml of triethylamine are dissolved in 2100 ml of absolute ethanol, and 182 g of chlorine are passed in while cooling at 20°–30°C. The solution is stirred for 1 ¼ hours at room temperature, after which the triethylamine hydrochloride is filtered off. The filtrate is concentrated in a rotary evaporator, the residue dissolved in 1000 ml of ether and 1000 ml of water are added. The phases are separated and the aqueous phase is extracted 3 times with 300 ml of ether each time. The ether phase is dried and concentrated. The residue is recrystallised from ligroin/xylene. Yield: 104.7 g (34 % of theory); m.p. 84°–86°C.

The following compounds are manufactured in analogous manner:

1-methyl-3-hydroxy-3-chloro-1,2,4-triazole
1-n-propyl-3-hydroxy-5-chloro-1,2,4-triazole; m.p. 26°–30°C
1-n-butyl-3-hydroxy-5-chloro-1,2,4-triazole; m.p. 41°–45°C
1-sec.-butyl-3-hydroxy-5-chloro-1,2,4-triazole; m.p. 77°–79°C
1-n-pentyl-3-hydroxy-5-chloro-1,2,4-triazole
1-sec.-pentyl-3-hydroxy-5-chloro-1,2,4-triazole; m.p. 25°–35°C
1-n-hexyl-3-hydroxy-5-chloro-1,2,4-triazole
1-(2',2',2'-trimethyl-propyl-3-hydroxy-5-chloro-1,2,4-triazole; m.p. 154°–160°C
cyclopentyl-5-chloro-1,2,4-triazole m.p. 128–130°C
cyclophenyl-5-chloro-1,2,4-triazole
1-(1'-methyl-decyl)-3-hydroxy-5-chloro-1,2,4-triazole
1-(1'-n-nonyl-decyl)-3-hydroxy-5-chloro-1,2,4-triazole
1-penyl-3-hydroxy-5-chloro-1,2,4-triazole; m.p. 139°–141°C
1-(n-phenylethyl)-3-hydroxy-5-chloro-1,2,4-triazole; m.p. 112°–114°C
1-(diphenylmethyl)-3-hydroxy-5-chloro-1,2,4-triazole
1-(2'-chlorophenyl)-3-hydroxy-5-chloro-1,2,4-triazole
1-(3'-chlorophenyl)-3-hydroxy-5-chloro-1,2,4-triazole 1-(4'-chlorophenyl)-3-hydroxy-5-chloro-1,2,4-triazole
1-(2',5'-dichlorophenyl)-5-hydroxy-5-chloro-1,2,4-triazole; m.p. 153-158°C
1-(3',5'-dichlorophenyl)-3-hydroxy-5-chloro-1,2,4-triazole
1-(3',4'-dichlorophenyl)-3-hydroxy-5-chloro-1,2,4-triazole
1-(2,4'-dichlorophenyl)-3-hydroxy-5-chloro-1,2,4-triazole
1-(2',4',5'-trichlorophenyl)-3-hydroxy-5-chloro-1,2,4-triazole
1-(4'-bromo phenyl)-3-hydroxy-5-chloro-1,2,4-triazole
1-(4'-fluorophenyl)-3-hydroxy-5-chloro-1,2,4-briazole
1-(2',3',4',5',6'-pentafluorophenyl)-3-hydroxy-5-chloro-1,2,4-triazole
1-(3'-tolyl)-3-hydroxy-5-chloro-1,2,4-triazole
1-(4'-tolyl)-3-hydroxy-5-chloro-1,2,4-triazole
1-(3'-chloro-4'-tolyl)-3-hydroxy-5-chloro-1,2,4-triazole
1-(3'-trifluoromethyl-phenyl)-3-hydroxy-5-chloro-1,2,4-triazole
1-(4'-methylmercapto-phenyl)-3-hydroxy-5-chloro-1,2,4-triazole
1-(4'-methanesulphinyl-phenyl)-3-hydroxy-5-chloro-1,2,4-triazole
1-(4'-methanesulphonyl-phenyl)-3-hydroxy-5-chloro-1,2,4-triazole
1-(4'-ethoxyphenyl)-3-hydroxy-5-chloro-1,2,4-triazole
1-(3'-nitrophenyl)-3-hydroxy-5-chloro-1,2,4-triazole.

f. 1-isopropyl-5-bromo-3-hydroxy-1.2.4-triazole 63.9 g of 1-isopropyl-1,2,4-triazolyl-(3)-benzoate with a melting point of 55°–57°C (manufactured from 1-isopropyl-3-hydroxy-1,2,4-triazole and benzoyl chloride), 53.4 g of N-bromosuccinamide and 0.2 g of azoisobutyronitrile in 550 ml of carbon tetrachloride are heated together for 48 hours to reflux. After the reaction mixture has been cooled to 0°C, the precipitate which has formed is filtered off with suction and heated to 75°C in 600 ml of water. The undissolved portion is filtered off and dried in vacuo, to give 40 g of 1-isopropyl-5-bromo-1,2,4-triazolyl-(3)-benzoate in the form of crystals melting at 125°–130°C.

361 g of this intermediate product are treated with 1950 ml of 2n NaOH and the mixture is heated to 60°C. The solution is cooled to 20°C, filtered clear with activated charcoal over Hyflo, and the filtrate is acidified with 390 ml of concentrated hydrochloric acid in 2000 ml of water. White crystals of 1-isopropyl-3-bromo-5-hydroxy-1,2,4-triazole (m.p. 155°–157°C) are obtained.

g. 1-isopropyl-5-fluoro-3-hydroxy-1,2,4-triazole 16.2 g of 1-isopropyl-5-chloro-3-hydroxy-1,2,4-triazole, 29 g of dry potassium fluoride and 150 ml of sulpholane are heated together for 16 hours to 160°–200°C. The solvent is evaporated in a high vacuum and the residue then treated with 10 % acetic acid and extracted with ethyl acetate. The ethyl acetate is evaporated off and the residueal solid is recrystallised from water, in the process of which 1-isopropyl-5-fluoro-3-hydroxy-1,2,4-triazole is obtained in the form of white crystals with a melting point of 80°–95°C. The product can be recrystallised from an organic solvent in order to purify it further.

Manufacture of the new phosphorus compounds a. 0,0-diethyl-0-[1-isopropyl-5-chloro-1,2,4-triazolyl-(3)]-thiophosphate 22.5 g of 1-isopropyl-5-chloro-3-hydroxy-1,2,4-triazole and 19.3 g of potassium carbonate in 500 ml of methyl ethyl ketone are heated for 2 ½ hours to reflux and the mixture is then cooled to room temperature. In the course of 15 minutes 26.3 g of diethylthiophosphoric chloride are added dropwise and the solution is heated for 3 hours to reflux. It is cooled and the salts are filtered off with the aid of Hyflo and washed with methyl ethyl ketone. The clear filtrate is evaporated in vacuo. The residue is purified by chromatography over a short silica gel column with 2 % methanol in chloroform as eluant. The solvent is afterwards distilled off and the compound of the formula

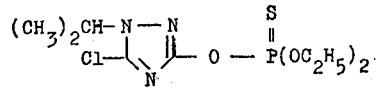

$n_D^{20}$: 1,4867 is obtained.

b. 0,0-diethyl-0-[1-phenyl-5-chloro-1,2,4-triazolyl-(3)]-thiophosphate 11.4 g of 1-phenyl-5-chloro-3-hydroxy-1,2,4-triazole and 8.0 g of potassium carbonate in 250 ml of methyl ethyl ketone are heated for 2 hours under reflux and the mixture is subsequently cooled to room temperature. 10.8 g of diethylthiophosphoric chloride are added dropwise and the solution is heated again for 1 ½ hours under reflux. It is then stirred overnight at room temperature. The salts are filtered off using Hyflo and the clear filtrate is evaporated in vacuo, to give the compound of the formula

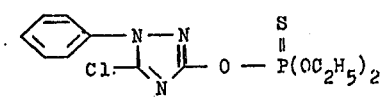

$n_D^{20}$: 1,5449.

c. 0-ethyl-0-[1-isopropyl-5-chloro-1,2,4-triazolyl-(3)]-methylaminothiophosphoric acid ester 32.2 g of 1-isopropyl-5-chloro-3-hydroxy-1,2,4-triazole and 27.6 g of potassium carbonate were heated under reflux for 2 hours in 400 ml of methyl ethyl ketone. The resulting slurry was cooled to room temperature and 34.7 g of O-ethyl-S-methylaminodithiophosphoric chloride in 100 ml of methyl ethyl ketone were added dropwise. The batch was heated to reflux once more for 2 hours and subsequently stirred over night at room temperature. The salts were filtered off using Hyflo and the solvent distilled off from the filtrate in vacuo. The residue was purified by chromatography over a short silica gel column with chloroform as eluant, giving the compound of the formula

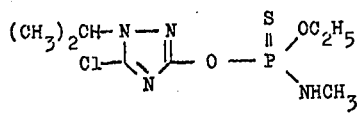

$n_D^{20}$: 1,5130.

d. 0,0-dimethyl-0-[1-isopropyl-5-chloro-1,2,4-triazolyl-(3)]-thiophosphate 33 g of 1-isopropyl-5-chloro-3-hydroxy-1,2,4-triazole and 27 g of potassium carbonate are heated under reflux for 2 hours in 400 ml of methyl ethyl ketone. The solution is cooled to room temperature and 32 g of dimethylthiophosphoric chloride are added dropwise. The batch is subsequently stirred for 5 hours at 60°C and stirring is continued overnight at room temperature. The salts are filtered off and the filtrate is concentrated in vacuo. The oily residue is purified by chromatography over a short silica gel column with chloroform as eluant, to give the compound of the formula

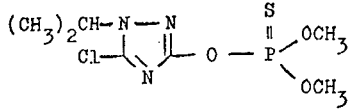

$n_D^{20}$: 1,4970.

e. 0,0-dimethyl-0-[1-isopropyl-5-chloro-1,2,4-triazolyl-(3)]-phosphate 32.2 g of 1-isopropyl-3-chloro-5-hydroxy-1,2,4-triazole and 27.6 g of potassium carbonate are heated under reflux for 2 hours in 400 ml of methyl ethyl ketone and the mixture is subsequently cooled to room temperature. 28.9 g of dimethylphosphoric chloride in 100 ml of methyl ethyl ketone are added dropwise and the solution is heated again under reflux for 2 hours. The batch is then stirred overnight at room temperature. The salts are then filtered off using Hyflo and the filtrate is concentrated in vacuo. The oily, dark residue is purified by chromatography over a short silica gel column with chloroform/1 % methanol, to give the compound of the formula

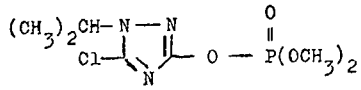

$n_D^{20}$: 1,4650.

The following compounds are also manufactured in analogous manner:

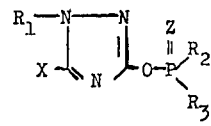

| $R_1$ | $R_3$ | $R_2$ | X | Z | Physical Data |
|---|---|---|---|---|---|
| ⟨phenyl⟩ | —OC$_2$H$_5$ | —NH—CH(CH$_3$)$_2$ | Cl | O | $n_D$20 : 1,5273 |
| —C$_3$H$_{7(i)}$ | —OC$_2$H$_5$ | —NH—CH(CH$_3$)$_2$ | Cl | 3. | Smp. : 50–52°C |
| —C$_3$H$_{7(i)}$ | —OC$_2$H$_5$ | —N(CH$_3$)$_2$ | Cl | S | $n_D$20 : 1,5016 |
| —C$_3$H$_{7(i)}$ | —OC$_2$H$_5$ | —NHCH$_3$ | Br | S | $n_D$20 : 1,5237 |
| —C$_3$H$_{7(i)}$ | —OC$_2$H$_5$ | —NH$_2$ | Cl | S | $n_D$20 : 1,5192 |
| —CH(CH$_3$)(C$_4$H$_9$(tert)) | —OC$_2$H$_5$ | —NHCH$_3$ | C. | S | $n_D$20 : 1,4988 |
| —C$_2$H$_5$ | —OC$_2$H$_5$ | —OC$_2$H$_5$ | Cl | S | $n_D$20 : 1,5032 |
| —C$_4$H$_{9(sek.)}$ | —OC$_2$H$_5$ | —OC$_2$H$_5$ | Cl | S | $n_D$20 : 1,4871 |
| —C$_4$H$_{9(i)}$ | —OC$_2$H$_5$ | —OC$_2$H$_5$ | Cl | S | $n_D$20 : 1,4882 |
| —C$_2$H$_5$ | —OCH$_3$ | —OCH$_3$ | Cl | S | $n_D$20 : 1,4939 |
| —C$_4$H$_9$(sek.) | —OCH$_3$ | —OCH$_3$ | Cl | S | $n_D$20 : 1,4953 |
| —C$_4$H$_{9(i)}$ | —OCH$_3$ | —OCH$_3$ | Cl | S | $n_D$20 : 1,4966 |
| ⟨phenyl⟩ | —OCH$_3$ | —OCH$_3$ | Cl | S | $n_D$20 : 1,5666 |
| —C$_3$H$_{7(i)}$ | —C$_2$H$_5$ | —OC$_2$H$_5$ | Cl | S | $n_D$20 : 1,4968 |
| —C$_3$H$_{7(i)}$ | —CH$_3$ | —OC$_3$H$_{7(n)}$ | Cl | S | $n_D$20 : 1,500 |
| -C$_3$H$_{7(i)}$ | ⟨phenyl⟩ | —OC$_2$H$_5$ | Cl | S | $n_D$20 : 1,5498 |
| —C$_4$H$_{9(sek.)}$ | —C$_2$H$_5$ | —OC$_2$H$_5$ | Cl | S | $n_D$20 : 1,5002 |
| —C$_4$H$_{9(i)}$ | —CH$_3$ | —OC$_2$H$_5$ | Cl | S | $n_D$20 : 1,4992 |
| ⟨phenyl⟩ | —C$_2$H$_5$ | —OC$_2$H$_5$ | Cl | S | $n_D$ 20 : 1,5620 |
| —C$_3$H$_{7(i)}$ | —OC$_2$H$_5$ | —OC$_2$H$_5$ | Cl | O | $n_D$20 : 1,4604 |
| —C$_3$H$_{7(i)}$ | —OC$_2$H$_5$ | —SC$_3$H$_{7(n)}$ | Cl | O | $n_D$20 : 1,4931 |
| —C$_3$H$_{7(i)}$ | —OC$_2$H$_5$ | —SC$_3$H$_{7(n)}$ | Cl | S | $n_D$20 : 1,5243 |
| —C$_3$H$_{7(i)}$ | —OC$_2$H$_5$ | —OC$_2$H$_5$ | Br | S | $n_D$20 : 1,4977 |
| —C$_3$H$_{7(i)}$ | —DCH$_3$ | —OC$_2$H$_5$ | Cl | S | $n_D$20 : 1,4888 |
| —C$_3$H$_{7(i)}$ | —OCH$_3$ | —OCH$_3$ | Br | S | $n_D$20 : 1,5133 |
| —C$_3$H$_{7(i)}$ | —CH$_3$ | —OC$_3$H$_{7(n)}$ | Br | S | $n_D$20 : 1,5135 |
| —C$_2$H$_5$ | —C$_2$H$_5$ | —OC$_2$H$_5$ | Cl | S | $n_D$20 : 1,5087 |
| —C$_4$H$_{9(n)}$ | —OC$_2$H$_5$ | —OC$_2$H$_5$ | Cl | S | $n_D$20 : 1,4896 |
| —C$_4$H$_{9(n)}$ | —C$_2$H$_5$ | —OC$_2$H$_5$ | Cl | S | $n_D$20 : 1,5017 |
| —C$_4$H$_{9(sek.)}$ | —OC$_2$H$_5$ | —OC$_2$H$_5$ | Cl | S | $n_D$20 : 1,4858 |
| —C$_4$H$_{9(sek.)}$ | — OCH$_3$ | —OCH$_3$ | Cl | S | $n_D$20 : 1,4919 |
| —CH(CH$_3$)(C$_4$H$_{9(tert.)}$) | —OC$_2$H$_5$ | —OC$_2$H$_5$ | Cl | S | $n_D$20 : 1,4880 |
| —CH(CH$_3$)(C$_4$H$_{9(tert.)}$) | —OCH$_3$ | —OCH$_3$ | Cl | S | $n_D$20 : 1,4930 |
| ⟨H⟩ | —OC$_2$H$_5$ | —OC$_2$H$_5$ | Cl | S | $n_D$20 : 1,5044 |
| —CH(CH$_3$)(C$_4$H$_9$(tert.)) | —OC$_2$H$_5$ | —S—C$_3$H$_{7(n)}$ | Cl | S | $n_D$20 : 1,4971 |
| ⟨H⟩ | —OCH$_3$ | —OCH$_3$ | Cl | S |  |

-continued

| $R_1$ | $R_3$ | $R_2$ | X | Z | Physical Data |
|---|---|---|---|---|---|
| $-C_3H_{7(i)}$ | $-OC_2H_5$ | $-SCH_3$ | Cl | S | |
| $-C_4H_{9(sek.)}$ | $-OC_2H_5$ | $-SC_3H_{7(n)}$ | Cl | S | |
| $-C_3H_{7(i)}$ | $-OC_2H_5$ | $-SC_3H_{7(n)}$ | Cl | S | |
| $-C_3H_{7(n)}$ | $-OC_2H_5$ | $-OC_2H_5$ | Cl | S | |
| $-C_3H_{7(n)}$ | $-OCH_3$ | $-OCH_3$ | Cl | S | |
| $\langle\phantom{=}\rangle-CH_2-$ | $-OC_2H_5$ | $-OC_2H_5$ | Cl | S | $n_D20 : 1,5344$ |
| $\langle\phantom{=}\rangle-CH_2-$ | $-OCH_3$ | $-OCH_3$ | Cl | S | $n_D20 : 1,5498$ |
| $\langle\phantom{=}\rangle-CH_2-$ | $-OC_2H_5$ | $-NHCH_3$ | Cl | S | $n_D20 : 1,554$ |
| $\langle\phantom{=}\rangle-CH_2-$ | $-OC_2H_5$ | $-SC_3H_{7(n)}$ | Cl | S | $n_D20 : 1,5648$ |
| $\langle\phantom{=}\rangle-CH(CH_3)-$ | $-OC_2H_5$ | $-OC_2H_5$ | Cl | S | $n_D20 : 1,5289$ |
| $\langle\phantom{=}\rangle-CH(CH_3)-$ | $-OCH_3$ | $-OCH_3$ | Cl | S | $n_D20 : 1,5437$ |
| $\langle\phantom{=}\rangle-CH(CH_3)-$ | $-OC_2H_5$ | $-NHCH_3$ | Cl | S | $n_D20 : 1,5517$ |
| $\langle\phantom{=}\rangle-CH(CH_3)-$ | $-OC_2H_5$ | $-SC_3H_{7(n)}$ | Cl | S | $n_D20 : 1,5590$ |
| $\langle\phantom{=}\rangle-CH(-\langle\phantom{=}\rangle)-$ | $-OC_2H_5$ | $-OC_2H_5$ | Cl | S | |
| $\langle\phantom{=}\rangle-CH(-\langle\phantom{=}\rangle)-$ | $-OCH_3$ | $OCH_3$ | Cl | S | |
| $\langle\phantom{=}\rangle-CH(-\langle\phantom{=}\rangle)-$ | $-C_2H_5$ | $-OC_2H_5$ | Cl | S | |
| $\langle\phantom{=}\rangle(CF_3)-$ | $-OC_2H_5$ | $-OC_2H_5$ | Cl | S | |
| $\langle\phantom{=}\rangle-$ | $-OC_2H_5$ | $-NHCH_3$ | Cl | S | m.p. : 51–59°C |
| $-C_3H_{7(i)}$ | $-OC_2H_5$ | $-NH-CH(CH_3)_2$ | Cl | O | m.p. : 53–56° |

EXAMPLE 2

A. Insecticidal ingest poison action

Tobacco and potato plants were sprayed with a 0.05% aqueous emulsion (obtained from a 10% emulsifiable concentrate).

After the coating had dried, the tobacco plants were populated with Egyptian cotton lead worms (*Spodoptera littoralis*) and the potato plants with Colorado potato bettle larvae (*Leptinotarsa decemlineata*). The test was carried out at 24°C and 60 % relative humidity. In the above test, the compounds according to Example 1 displayed ingest poison action against Spodoptera littoralis and Leptinotarsa decemlineata.

B. Systemic insecticidal action

To determine the systemic action, rooted bean plants (*Vicia fabae*) were put into a 0.01% aqueous active substance solution (obtained from a 10% emulsifiable concentrate). After 24 hours, aphids (*Aphis fabae*) were placed on the parts of the plant above the soil.

The aphids were protected from contact and gas action by means of a special device. The test was carried out at 24°C and 70% relative humidity. In the above tests the compounds according to Example I displayed good insecticidal ingest poison action and systemic insecticidal action.

EXAMPLE 3

Action against *Chilo suppressalis*

Six rice plants at a time of the variety Caloro were transplanted into plastic pots (diameter at the top = 17 cm) and reared to a height of about 60 cm. Infestation with Chilo suppressalis larvae ($L_1$: 3–4 mm long) took place 2 days after the active substance had been applied in granule form to the paddy water (rate of application: 8 kg of active substance per hectare). Evaluation of the insecticidal action took place 10 days after application of the granules.

The compounds according to Example I were active in the above test against Chilo suppressalis.

EXAMPLE 4

Action against *Aulacophera femoralis*, Pachmoda and Chortophila larvae

Sterilised compost earth was homogeneously mixed with a wettable powder containing 25% of active substance so that there resulted a rate of application of 8 kg of active substance per hectare.

Young zucchetti plants (*Cucumis pepo*) were put into plastic pots with the treated soil (3 plants per pot; diameter of pot = 7 cm). Each pot was infected immediately afterwards with 5 *Aulacophora femoralis* and Pachmoda or Chortophila larvae. The control was carried out 4, 8, 16 and 32 days after depositing the larvae.

At 80–100% kill after the first control, a fresh infestation with 5 larvae each was carried out in the same soil sample with 3 new zucchetti plants. If the activity was less than 80%, the remaining larvae remained in the soil sample until the control immediately following. If an active substance at a rate of application of 8 kg/ha still effected a 100% kill, a further control with 4 and 2 kg of active substance per hectare was carried out.

In the above test, the compounds according to Example I displayed action against *Aulacophora fermoralis*, Pachmoda and Chortophila larvae.

EXAMPLE 5

Action against ticks

A. *Rhicephalus bursa*

Five adult ticks and 50 tick larvae were counted into a glass tube and immersed for 1 to 2 minutes in 2 ml of an aqueous emulsion from an emulsion series each containing 100, 10, 1 and 0.1 ppm of test substance. The tube was then sealed with a standardised cotton wool plug and placed on its head, so that the active substance emulsion could be adsorbed by the cotton wool.

In the case of the adults evaluation took place after 2 weeks, and in that of the larvae after 2 days. Each test was repeated twice.

B. *Boophilus microplus* (larvae)

Tests were carried out in each case with 20 OP-sensitive larvae using an analogous dilution series as in the case of test A. (The resistance refers to the tolerability of Diazinon).

The compounds according to Example 1 acted in the above test against adults and larvae of *Rhipicephalus bursa* and sensitive and OP-resistant larvae of *Boophilus microplus*.

EXAMPLE 6

Acaracidal action

*Phaseolus vulgaris* (dwarf beans) have an infested piece of leaf from a mass culture of *Tetranychus urticae* placed on them 12 hours before the test for the acaricidal action. The mobile stages which have migrated are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "interim", the treated plants are kept in greenhouse compartments at 25°C.

The compounds according to Example I are active in the above test against eggs, larvae and adults of *Tetranychus urticae*.

EXAMPLE 7

Action against soil nematodes

To test the action against soil nematodes, the active substance (in the concentration indicated in each case is applied to and intimately mixed with soil infected with root gall nematodes (*Meloidgyne avenaria*). Immediately afterwards, tomato cuttings are planted in the thus prepared soil in a series of tests and after a waiting time of 8 days tomato seeds are sown in another test series.

In order to assess the nematocidal action, the galls present on the roots are counted 28 days after planting and sowing respectively. The compounds according to Example I display good action against *Meloidgyne avenaria*.

We claim:

1. An insecticidal, acaricidal and nematocidal composition comprising an insecticidally, acaricidally and nematocidally effective amount of a compound of the formula $$R_1-N \underset{\underset{N}{\parallel}}{\overset{}{\underset{X}{\diagdown}}} N \underset{}{\overset{Z}{\underset{\parallel}{-}}} O-P\overset{R_2}{\underset{R_3}{\diagdown}}$$

wherein X represents fluorine, chlorine or bromine; Z represents oxygen or sulphur; $R_1$ represents $C_1$-$C_{19}$ alkyl, $C_3$-$C_8$ cycloalkyl, or phenyl, benzyl, phenylethyl, diphenylmethyl or optionally substituted by halogen, nitro, alkyl, haloalkyl, alkoxy, alkylsulphinyl or alkylsulphonyl, the alkyl groups of which each have 1–6 carbon atoms; $R_2$ represents $C_1$-$C_{19}$ alkoxy, $C_1$-$C_{19}$ alkylthio, amino, mono- or di($C_1$-$C_{19}$)alkylamino; and $R_3$ represents $C_1$-$C_{19}$ alkyl, $C_1$-$C_{19}$ alkoxy, $C_1$-$C_{19}$ alkylthio, phenyl, phenoxy, amino, mono- or di(C₁-C₁₉)alkylamino; together with a suitable carrier therefor.

2. The composition of claim 1, wherein in said compound X represents chlorine or bromine; Z represents oxygen or sulphur, R₁ represents alkyl having 1 to 19 carbon atoms, cyclopentyl, phenylethyl, diphenylmethyl or

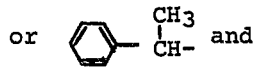

and phenyl or benzyl which is unsubstituted or substituted by fluorine, chlorine, bromine, methyl, trifluoromethyl, methoxy, methylthio, ethoxy or nitro; R₂ represents methoxy, ethoxy, propoxy, 2-chloroethoxy, propylthio, methylamino, dimethylamino or isopropylamino; and R₃ represents methyl, ethyl, methoxy, methylthio, ethoxy, ethylthio, propoxy, 2-chloroethyl, propylthio, phenyl, phenoxy, amino, methylamino or dimethylamino.

3. The composition of claim 2, wherein in said compound X represents chlorine, Z represents sulphur, R₁ represents alkyl, with 1 to 6 carbon atoms, cyclopentyl, phenyl, 3-trifluoromethylphenyl, benzyl, diphenylmethyl or

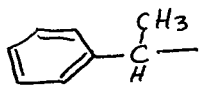

R₂ represents methoxy, ethoxy or propoxy, R₃ represents methyl, ethyl, methoxy, ethoxy, propylthio, amino, methylamino and dimethylamino.

4. The composition of claim 3, wherein said compound is 0,0-diethyl-0-[1-isopropyl-5-chloro-1,2,4-triazolyl-(3)]-thiophosphate.

5. The composition of claim 3, wherein said compound is 0,0-diethyl-0-[1-ethyl-5-chloro-1,2,4-triazolyl-(3)]-thiophosphate.

6. The composition of claim 3, wherein said compound is 0-ethyl-S-propyl-0-[1-isopropyl-5-chloro-1,2,4-triazolyl-(3)]-dithiophosphate.

7. The composition of claim 3, wherein said compound is 0-ethyl-S-propyl-0-[1-benzyl-5-chloro-1,2,4-triazolyl-(3)]dithiophosphate.

8. A method for combatting insects, acaricides or nematodes which comprises applying thereto an insecticidally, acaricidally, or nematocidally effective amount of a compound of the formula of claim 1.

9. A method for combatting insects, acaricides or nematodes which comprises applying thereto an insecticidally, acaricidally or nematocidally effective amount of the compound of claim 2.

10. A method for combatting insects, acaricides or nematodes which comprises applying thereto an insecticidally, acaricidally or nematocidally effective amount of the compound of claim 3.

* * * * *

UNITED STATES PATENT AND TRADEMARK OFFICE
CERTIFICATE OF CORRECTION

PATENT NO. : 3,932,629
DATED : January 13, 1976
INVENTOR(S) : Dag Dawes et al.

It is certified that error appears in the above—identified patent and that said Letters Patent are hereby corrected as shown below:

Title Page, Item [30], change

"Sept. 29, 1972   Switzerland............14254/72" to

-- Oct. 6, 1972   Switzerland............14693/72 --

Signed and Sealed this

Twenty-sixth Day of October 1976

[SEAL]

*Attest:*

RUTH C. MASON
*Attesting Officer*

C. MARSHALL DANN
*Commissioner of Patents and Trademarks*